United States Patent [19]
Yoshimoto et al.

[11] Patent Number: 5,534,709
[45] Date of Patent: Jul. 9, 1996

[54] RADIATION IMAGE READING APPARATUS

[75] Inventors: Shinichi Yoshimoto; Fumihiro Namiki, both of Kawasaki, Japan

[73] Assignee: Fujitsu Limited, Kawasaki, Japan

[21] Appl. No.: 299,109

[22] Filed: Sep. 2, 1994

[30] Foreign Application Priority Data

Oct. 7, 1993 [JP] Japan .................................. 5-251345

[51] Int. Cl.⁶ .................................................. G01N 23/04
[52] U.S. Cl. .................................................... 250/588
[58] Field of Search ............................................. 250/588

[56] References Cited

U.S. PATENT DOCUMENTS

| | | | |
|---|---|---|---|
| 3,859,527 | 1/1975 | Luckey | 250/327 |
| 4,496,838 | 1/1985 | Umemoto et al. | 250/588 |
| 5,021,671 | 6/1991 | Kohda | 250/484.4 |
| 5,038,037 | 8/1991 | Saotome | 250/588 |

FOREIGN PATENT DOCUMENTS 61-258562  11/1986  Japan .
2272440  11/1990  Japan ........................ 250/588

*Primary Examiner*—Carolyn E. Fields
*Attorney, Agent, or Firm*—Staas & Halsey

[57] ABSTRACT

In a radiation image reading apparatus, a photostimulated phosphor member absorbs a portion of radiation energy transmitted through an object and stores the absorbed radiation energy as a latent image. An excitation light source irradiates excitation light on the photostimulated phosphor member which then emits photostimulated luminescence light which is received and converged by an image reading device, and the latter outputting, as image information, an electrical signal which is dependent on a light intensity of the photostimulated luminescence light. A source of erasing light, having a spectral distribution band positioned substantially in a visible light region and which is normally ON, includes a shutter which is selectively opened to irradiate the erasing light on the photostimulated phosphor during an erasure time and otherwise is closed. A moving mechanism relatively moves the excitation light source and the image reading device with respect to the photostimulated phosphor member, in a moving direction which is perpendicular to the main scan direction.

22 Claims, 15 Drawing Sheets

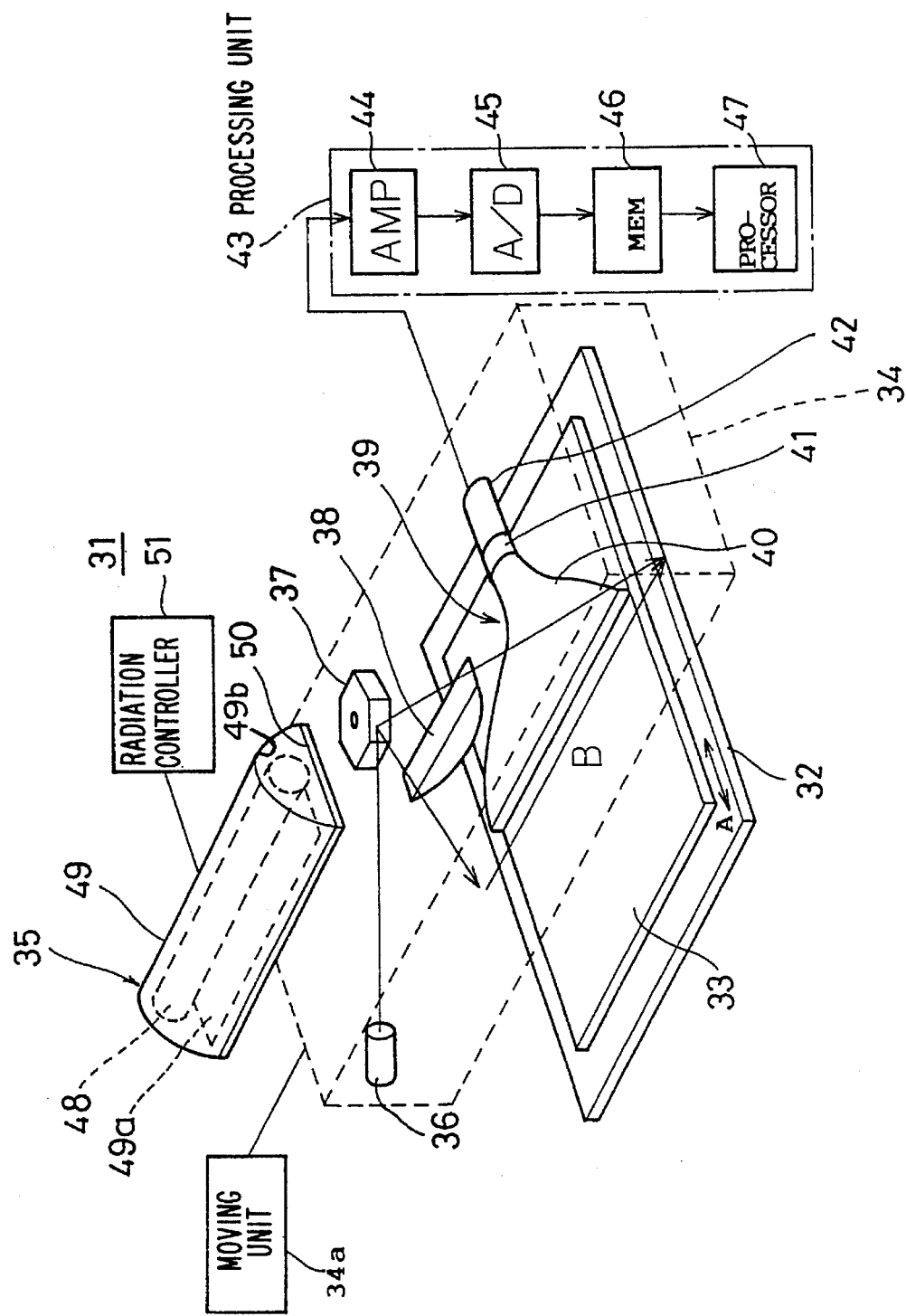

RADIATION IMAGE READING APPARATUS

BACKGROUND OF THE INVENTION

1. Field of the Invention

The present invention generally relates to radiation image reading apparatuses and, more particularly, to a radiation image reading apparatus which stores radiation image information in a photostimulated phosphor and reads the image information by photostimulated luminescence light.

2. State of the Prior Art

Recently, radiation images such as x-ray images are widely used for making disease diagnosis. Conventionally, the so-called radiation photography is used as a means of obtaining the x-ray image. In other words, the x-ray transmitted through an object (for example, a patient) is irradiated on a phosphor layer or screen so as to generate visible light, and this visible light is irradiated on a silver film and developed.

On the other hand, as an x-ray image pickup system which can realize high sensitivity and high resolution, a technique which uses a photostimulated phosphor has been proposed to replace the conventional technique of recording a 2-dimensional radiation image directly or indirectly on a film which is made up of a sheet which is coated with a silver (silver chloride) sensitive agent.

The basic method of using the photostimulated phosphor is proposed in a U.S. Pat. No. 3,859,523. According to this proposed method, the photostimulated phosphor is made of $BaBr_2$:Eu, for example. When the photostimulated phosphor receives a radiation energy of the x-ray or the like, this energy is stored in the crystals of the photostimulated phosphor in a relatively stable storage state. The energy is stored in the photostimulated phosphor for a long or relatively long time.

When a first light, which acts as an excitation light, is irradiated on this photostimulated phosphor in this state Where the energy is stored therein, photostimulated luminescence light having an intensity corresponding to the stored energy is emitted from the phosphor as a second light.

In this case, the first light is not limited to visible light, and light having a wide range of wavelengths from the infrared ray to the ultraviolet ray, may be selected and used. This selection differs depending on the phosphor material. The second light may also range from the infrared ray to the ultraviolet ray, and the particular kind of second light depends on the phosphor material.

On the other hand, an x-ray image pickup system has been proposed that utilizes the characteristics of the photostimulated phosphor. According to the x-ray image pickup system, the radiation transmitted through the object, such as the patient, is irradiated on the photostimulated phosphor and recorded thereon, so that radiation image information is obtained.

More particularly, excitation light such as a laser beam scans the photostimulated phosphor plate (or sheet) which stores the x-ray information related to the object, so as to generate photostimulated luminescence light. This photostimulated luminescence light is converged and converted in a photoelectric converter, to obtain an electrical signal proportional to the intensity of the stored radiation. Thereafter, an image processing is carried out with respect to this electrical signal. In other words, a visualized radiation image is obtained by printing the image on a silver film or displaying the image on a cathode ray tube (CRT).

After the photostimulated luminescence light is generated by using the excitation laser beam, radiation energy still remains within the photostimulated phosphor plate. Hence, strong excitation light is irradiated on the photostimulated phosphor plate to eliminate the residual energy by generating photostimulated luminescence light. Then, the photostimulated phosphor plate again stores the x-ray information related to the object. Hence, the recording of the x-ray information, up to the erasure of the residual energy, corresponds to one processing cycle of the read apparatus, and such a processing cycle is repeated.

SUMMARY OF THE INVENTION

To better understand the invention, a conceptual development of the present inventors, termed a "conceivable radiation image reading apparatus" is first described.

FIG. 1 shows the construction of the conceivable radiation image reading apparatus. In FIG. 1, a radiation image reading apparatus 11 has a photostimulated phosphor plate (or sheet) 13 placed on a precision stage 12. An creasing light source 14 for making an erasure, an excitation light irradiating system 15 and an optical guide path 16 are arranged above the photostimulated phosphor plate 13. The optical guide path 16 is made up of a predetermined number of bundled optical fibers.

The light source 14 is made up of a halogen lamp 14a having a length greater than or equal to a width of the photostimulated phosphor plate 13, for example, and a reflecting plate 14b. The excitation light irradiating system 15 is formed by an excitation light source 17, a rotary polygon mirror 18 and a condenser lens 19.

The optical guide path 16 has a light receiving end 16a and a light converging end 16b opposite to the light receiving end 16a. A photo-multiplier 20 is connected to the light converging end 16b of the optical guide path 16 via a filter 20a. An output of the photo-multiplier 20 is supplied to a pre-stage amplifier ("PREAMP") 21. An output of this pre-stage amplifier 21 is stored in an image memory 23 via an analog-to-digital (A/D) converter 22.

In the radiation image reading apparatus 11 having the above described construction, a laser beam emitted from the excitation light source 17, as an excitation light, is irradiated on the polygon mirror 18 and performed scanning via the condenser lens 19. The scan is made in a main scan direction which is perpendicular to a moving direction of the photostimulated phosphor plate 13. Accelerated phosphorescence light generated by one scan of the excitation light is converged by the optical guide path 16 and supplied to the photo-multiplier 20.

As described above, the filter 20a is provided between the optical guide path 16 and the photo-multiplier 20. This filter 20a selectively transmits light having the wavelength of the photostimulated luminescence light, so as not to transmit the light having the wavelength of the excitation light. The photostimulated luminescence light selectively obtained from the filter 20a is converted into an electrical signal in the photo-multiplier 20, and is amplified in the pre-stage amplifier 21 to a signal having an optimum level for the A/D converter 22. The A/D converter 22 digitizes the signal from the pre-stage amplifier 21, and stores digital image data in the image memory 23. The stored digital image data are thereafter subjected to the image processing, so as to output the image on the CRT (not shown) or output the image as a hard copy.

Next, light from the halogen lamp 14a irradiates the entire surface of the photostimulated phosphor plate 13 so as to erase or eliminate the residual radiation energy. Thereafter, the photostimulated phosphor plate 13 can be used again for storing radiation image information.

FIG. 2 is a graph showing the intensity of the photostimulated luminescence light generated from the photostimulated phosphor plate 13 shown in FIG. 1, and FIG. 3 is a graph showing the spectral distribution of the halogen lamp 14a shown in FIG. 1.

FIG. 2 shows a case where the photostimulated phosphor plate 13 is made of $BaBr_2:Eu$. The intensity of the photostimulated luminescence light is particularly high when the wavelength of the excitation light is in the visible light region, and is essentially zero in other regions.

On the other hand, in FIG. 3, the spectral distribution of the halogen lamp 14a spreads to the regions of the infrared ray and the ultraviolet ray other than (i.e., beyond) the visible light region. Only the light in the visible light region contributes to the erasure, and the light in the regions other than the visible light region does not directly contribute to the erasure. In addition, the light in the ultraviolet ray region causes re-excitation of the photostimulated phosphor plate 13 and further increases the residual energy level, thereby making the erasure difficult.

Accordingly, even if the halogen lamp 14a, as used, has a large power consumption, the efficiency of the erasure is poor, and the irradiation with respect to the photostimulated phosphor plate 13 must be made for a long time in order to reduce the residual energy level to a desired low level. Because of this long time required to carry out the erasure with respect to the photostimulated phosphor plate 13, the processing time of one cycle of the reading apparatus is affected thereby, and the processing speed of the reading apparatus becomes slow.

Generally, the efficiency of the erasure made by the erasing light source can be described by the total bundle of rays (lm/W) per unit power consumption, and is referred to as a lamp efficiency. The lamp efficiency of the halogen lamp is approximately 20 to 30 lm/W.

Hence, measures have been taken, such as providing a cooling apparatus and irradiating the light from the halogen lamp 14a on the photostimulated phosphor lamp 13 after transmitting the light through a filter, for cutting the ultraviolet ray and infrared ray.

However, the provision of the cooling apparatus or the filter for cutting the ultraviolet ray and infrared ray not only increases the production cost of the reading apparatus, but also makes the reading apparatus bulky and complex. In addition, the light from the halogen lamp 14a must be irradiated on the photostimulated phosphor plate 13 for a long time in order to reduce the residual energy to the desired level. In other words, the erasure time takes up most of the processing time of one cycle of the reading apparatus, and there is a problem in that the total processing time of the reading apparatus becomes long because of the long erasure time.

Accordingly, it is a general object of the present invention to provide a novel and useful radiation image reading apparatus in which the problems described above are eliminated.

Another and more specific object of the present invention is to provide a radiation image reading apparatus comprising a photostimulated phosphor absorbing a portion of radiation energy transmitted through an object and storing the radiation energy in a form of a latent image, an excitation light source irradiating excitation light on the photostimulated phosphor in a main scan direction so as to generate photostimulated luminescence light from the photostimulated phosphor, image reading means for converging the photostimulated luminescence light from the photostimulated phosphor and outputting as image information an electrical signal which is dependent on a light intensity of the photostimulated luminescence light, an erasing light source irradiating light for erasing residual radiation energy of remaining on the photostimulated phosphor at a time of an erasure after obtaining the image information by the image reading means, the light from the erasing light source having a major part of a spectral distribution thereof positioned in a visible light, region or its vicinity, and moving means for relatively moving the excitation light source and the image reading means with respect to the photostimulated phosphor in a moving direction which is perpendicular to the main scan direction, where the erasing light source includes at least one shutter which is opened to irradiate the light from the erasing light source on the photostimulated phosphor only at the time of the erasure. According to the radiation image reading apparatus of the present invention, it is possible to improve the efficiency of the erasure by irradiating the light in the visible light region for the erasure, because the photostimulated luminescence light generated from the photostimulated phosphor is strongest in the visible light region. In other words, it is unnecessary to irradiate the light for the erasure for a long time. As a result, it is possible to reduce the erasure time, and, accordingly, to reduce the processing time of the reading apparatus. In addition, it is possible to greatly reduce the amount of infrared ray and/or ultraviolet ray irradiated on the photostimulated phosphor by providing a filter through which the light for the erasure is emitted. By taking this measure, it is possible to prevent deterioration of the efficiency of erasure, and make it unnecessary to provide a cooling apparatus or the like.

Other objects and further features of the present invention will be apparent from the following detailed description when read in conjunction with the accompanying drawings.

BRIEF DESCRIPTION OF THE DRAWINGS

FIG. 4 is a perspective view generally showing a first embodiment of a radiation image reading apparatus according to the present invention;

DESCRIPTION OF THE PREFERRED EMBODIMENTS

Figure 1:
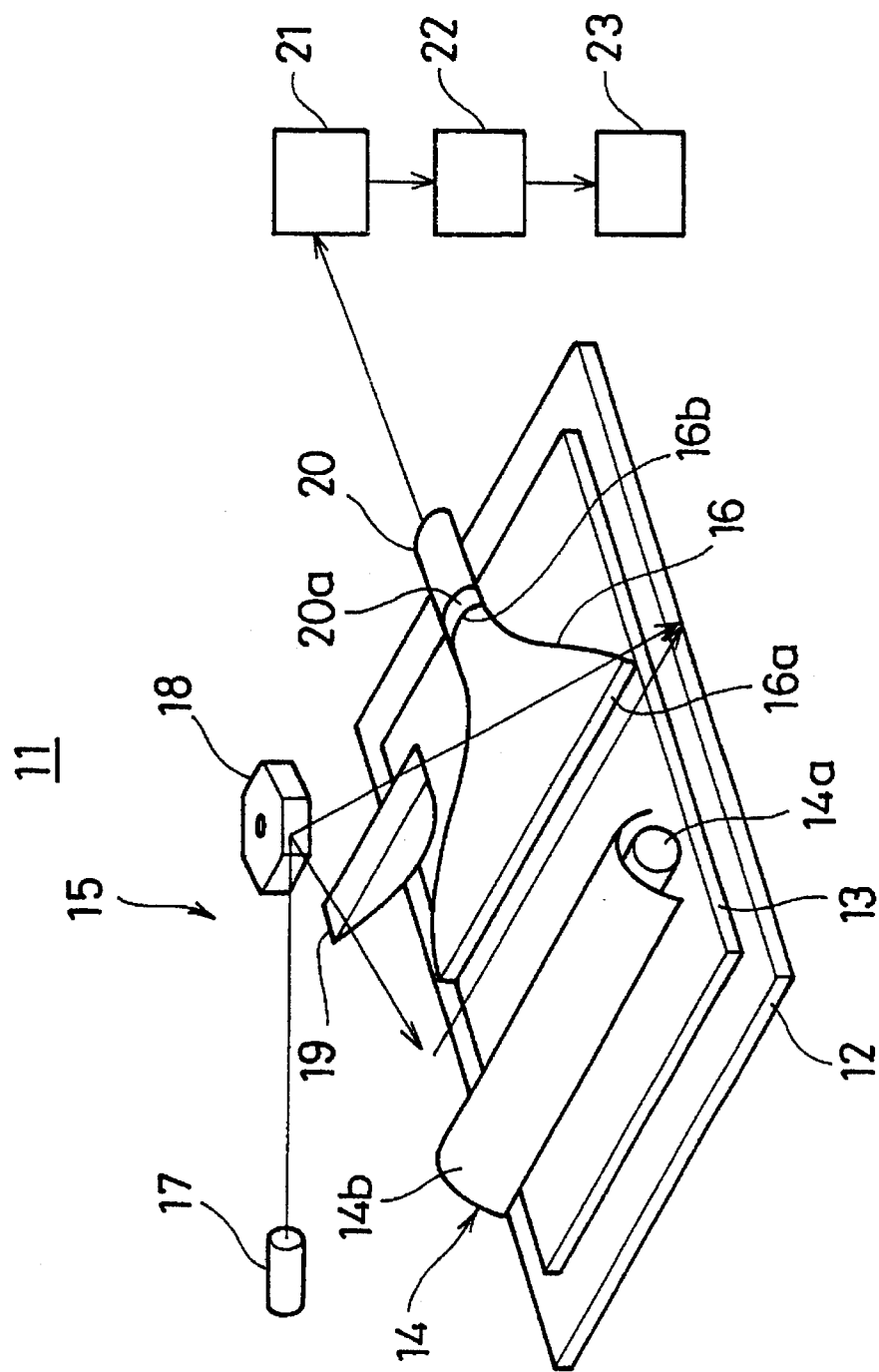
FIG. 1 is a perspective view generally showing a conceivable radiation image, reading apparatus.
Figure 2:
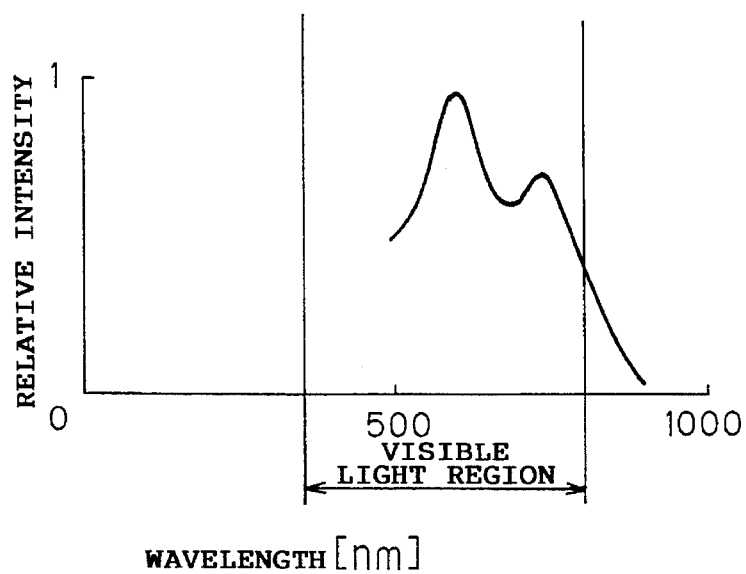
FIG. 2 is a graph showing the intensity of photostimulated luminescence light generated from a photostimulated phosphor plate shown in FIG. 1.
Figure 3:
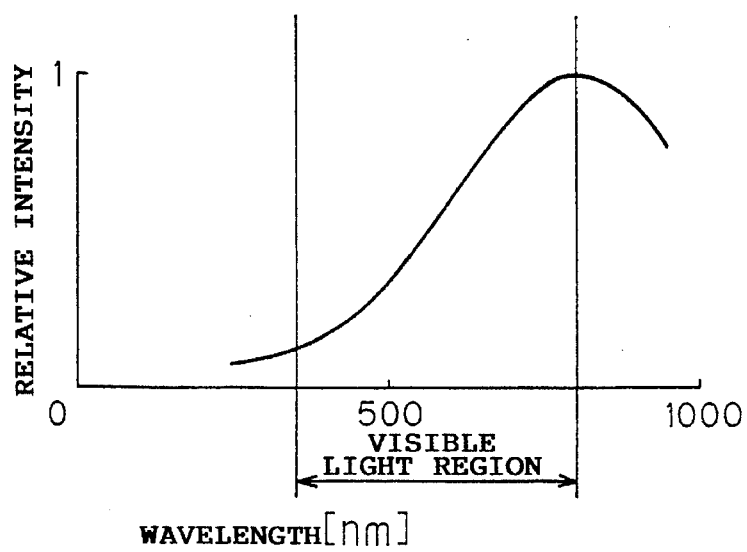
FIG. 3 is a graph showing the spectral distribution of a halogen lamp shown in FIG. 1.

FIG. 4 generally shows the construction of a first embodiment of a radiation image reading apparatus according to the present invention.

In FIG. 4, a radiation image reading apparatus 31 has a photostimulated phosphor plate (or sheet) 33 placed on a precision stage 32 which is movable in direction A. The photostimulated phosphor plate 33 is made of a $BaBr_2$:Eu composition, for example. This photostimulated phosphor plate 33 absorbs a portion of the radiation energy transmitted through an object and incident thereon, and stores the absorbed radiation energy as a latent image. Accelerated phosphorescence light is generated by the photostimulated phosphor plate 33 in response to an excitation light incident thereon.

An excitation light scan unit 34 is arranged above the photostimulated phosphor plate 33. In addition, an erasing light source 35 is arranged above the excitation light scan unit 34.

The excitation light scan unit 34 is comprises an excitation light source 36, a rotary polygon mirror 37, a lens 38 and an image reader means 39. A laser beam, emitted from the excitation light source 36 as the excitation light, is deflected by the polygon mirror 37 and is irradiated onto the photostimulated phosphor plate 33 via the lens 38. Hence, the excitation light scans the photostimulated phosphor plate 33 in a main scan direction B which is perpendicular to the moving direction A of the photostimulated phosphor plate 33. In addition, the image reading unit 39 comprises an optical guide path 40, a filter 41 and a photo-multiplier 42. The optical guide path 40 is made up of bundled optical fibers. One end of the optical guide path 40 is arranged along the main scan direction B of the photostimulated phosphor plate 33, and the other end of the optical guide path 40 is mounted on the photomultiplier 42. The excitation light scan unit 34 having the above described construction is movable back and forth in opposite directions A, perpendicular to the main scan direction B, by a moving unit 34a.

An output of the photo-multiplier 42 is supplied to a processing unit 43. This processing unit 43 includes an amplifier 44, an A/D converter 45, a memory 46 and an image processor 47.

Figure 7A:
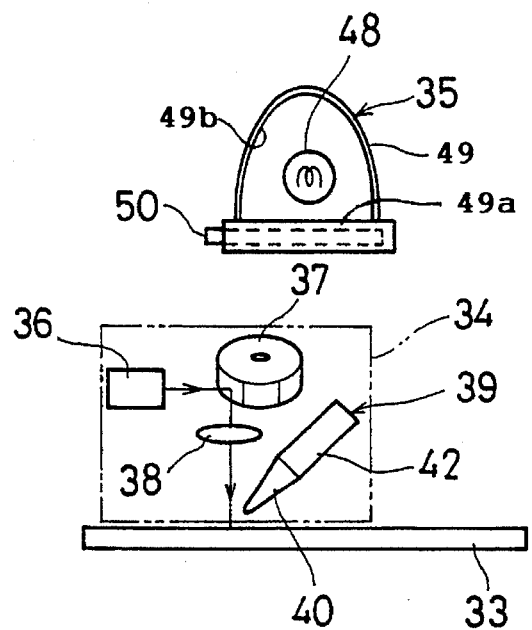
FIGS. 7A and 7B are diagrams for explaining the operation of the first embodiment.
Figure 7B:
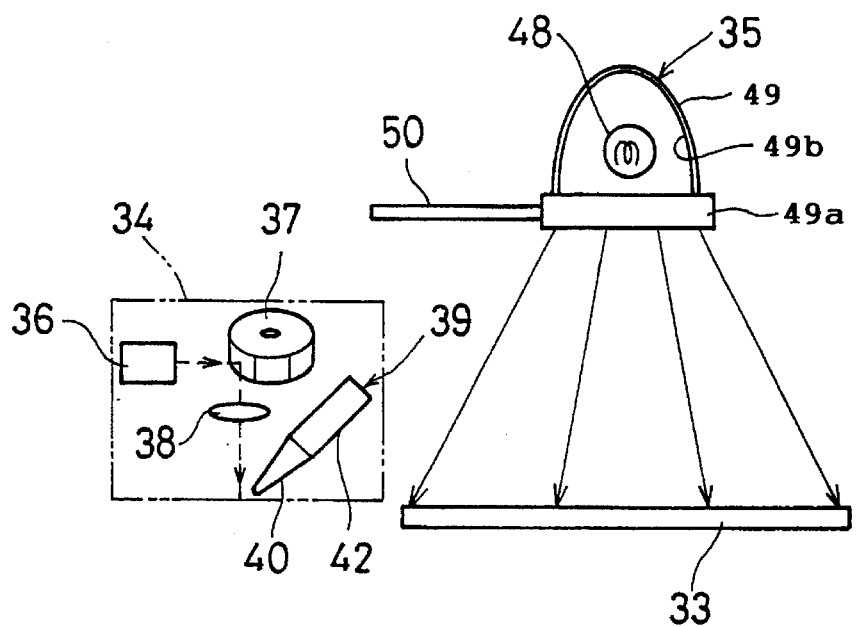

On the other hand, the erasing light source 35 includes a lamp 48, a light blocking member 49 and a shutter 50. The lamp 48 extends in a longitudinal direction matching the main scan direction B, and is provided on the inside of the light blocking member 49. This light blocking member 49 has a light emission opening 49a, and the shutter 50 is provided at the light emission opening 49a, as an opening and closing unit. A reflecting mirror 49b is provided on the inside of the light blocking member 49 for the purpose of improving the illumination efficiency, as also shown in FIGS. 7A and 7B and which will be described later. In addition, the illumination of the lamp 48 is controlled by an irradiation controller 51.

The lamp 48 emits light for erasing the residual radiation energy of the photostimulated phosphor plate 33, and a major portion of the spectral distribution of this light is located in the visible light region or its vicinity. For example, a high-pressure sodium lamp, a low-pressure sodium lamp, a metal halide lamp, a mercury lamp or the like are appropriately selected and used as the lamp 48.

Figure 5A:
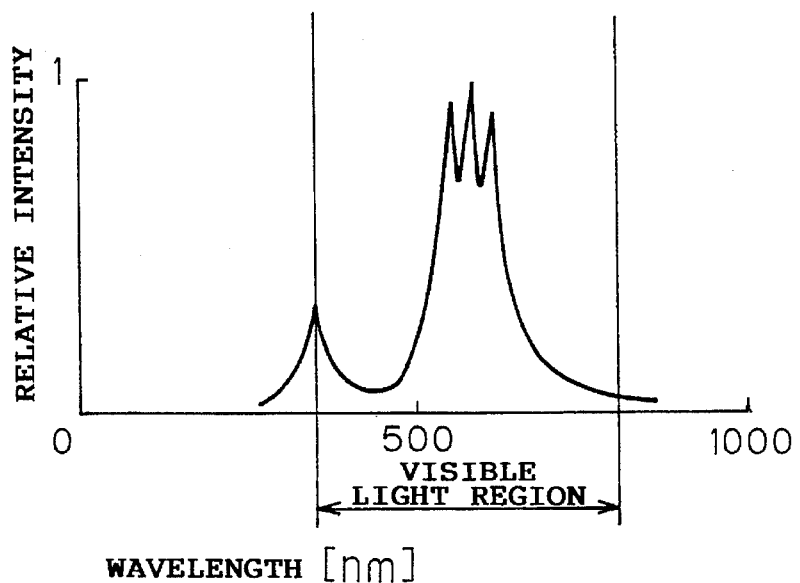
FIGS. 5A and 5B are graphs for explaining the spectral distribution of an erasing light source shown in FIG. 4.
Figure 5B:
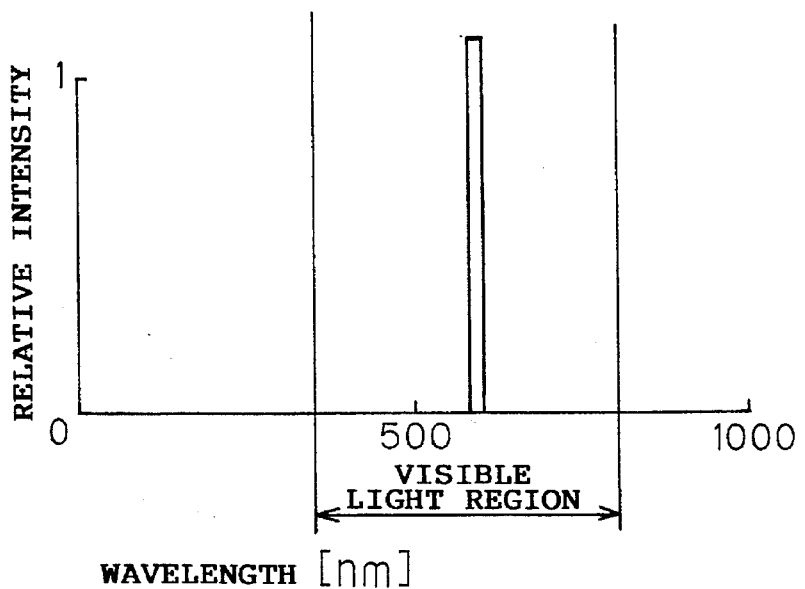
Figure 6A:
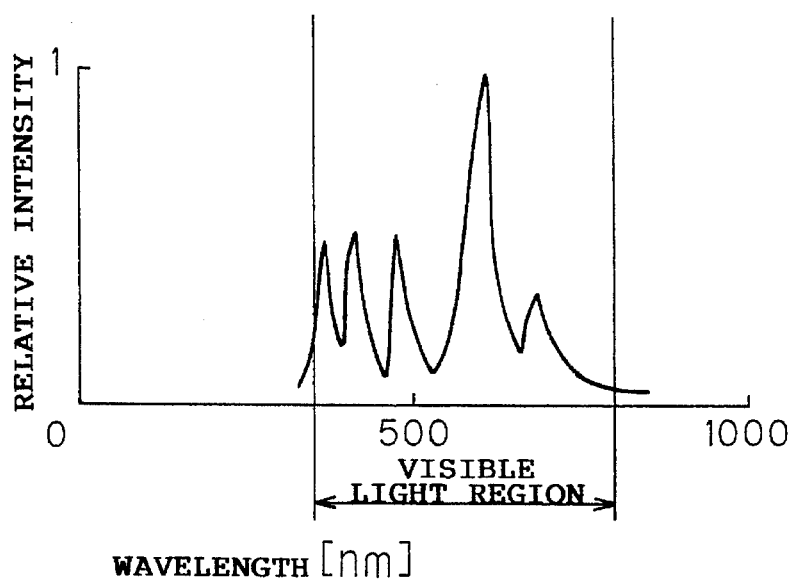
FIGS. 6A and 6B are graphs for explaining the spectral distribution of an erasing light source shown in FIG. 4.
Figure 6B:
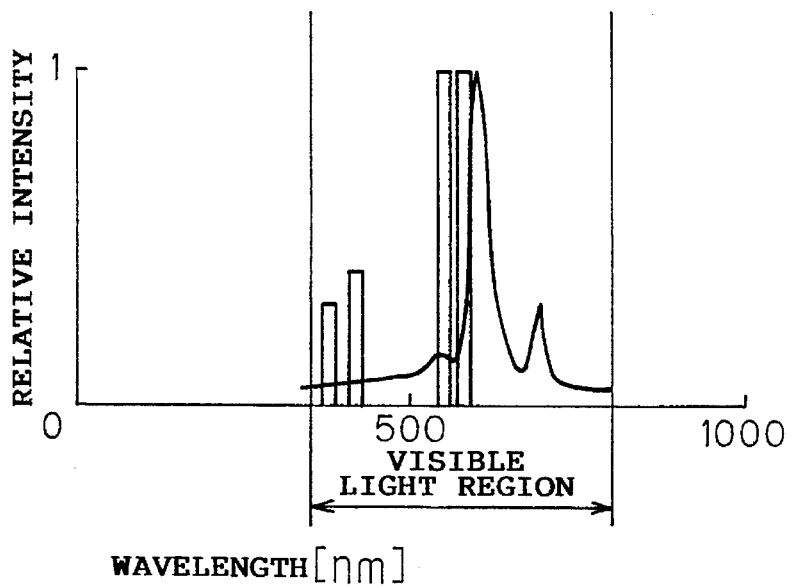

FIGS. 5A and 5B and FIGS. 6A and 6B are graphs showing the spectral distribution of the erasing light source 35 shown in FIG. 4. FIG. 5A shows the spectral distribution of the erasing light source 35 which uses a high-pressure sodium lamp as the lamp 48, and FIG. 5B shows the spectral distribution of the erasing light source 35 which uses a low-pressure sodium lamp as the lamp 48. The lamp efficiency of the high-pressure sodium lamp is 132 lm/W (360 W), and the lamp efficiency of the low-pressure sodium lamp is 175 lm/W (180 W). In addition, FIG. 6A shows the spectral distribution of the erasing light source 35 which uses a metal halide lamp as the lamp 48, and FIG. 6B shows the spectral distribution of the erasing light source 35 which uses a mercury lamp as the lamp 48. The lamp efficiency of the metal halide lamp is 95 lm/W (400 W), and lamp efficiency of the mercury lamp is 55 lm/W (400 W).

As shown in FIG. 5A, the spectral distribution of the high-pressure sodium lamp is in the range of 500 to 800 nm, and has a peak at 580 nm. In addition, since the low-pressure sodium lamp emits monochromatic light, the spectral distribution has a sharp peak at 580 nm. The major portions of the spectral distributions of both the high-pressure and the low-pressure sodium lamps are located within the visible light region, as shown in FIGS. 5A and 5B. The lamp efficiency of the high-pressure sodium lamp is approximately four times that of the halogen lamp, and the lamp efficiency of the low-pressure sodium lamp is approximately five times that of the halogen lamp.

Similarly, the major portions of the spectral distributions of both the metal halide lamp and the mercury lamp are located within the visible light region as shown in FIGS. 6A and 6B.

Therefore, the high-pressure sodium lamp, the low-pressure sodium lamp the metal halide lamp and the mercury lamp are suited for use as the lamp 48 of the first embodiment.

FIGS. 7A and 7B are diagrams for explaining the operation of the first embodiment shown in FIG. 4.

As shown in FIGS. 4 and 7A, the photostimulated phosphor plate 33 absorbs a portion of the radiation energy transmitted through the object and stores the energy in the form of a latent image. In addition, the excitation light scan unit 34 is positioned above the photostimulated phosphor plate 33 by the moving unit 34a.

The lamp 48 is constantly turned ON. However, at times other than the erasure, the lamp 48 is turned ON with a reduced power and the light emitted from the lamp 48 is blocked by the shutter 50 under the control of the irradiation controller 51. The lamp 48 is constantly turned ON because the lamps such as the high-pressure sodium lamp, the low-pressure sodium lamp, the metal halide lamp and the mercury lamp takes several minutes to stabilize after the discharge starts. In other words, it takes time for the lamp 48 to stabilize if the power is supplied to the lamp 48 every time the erasure is to be made, and the lamp 48 is constantly turned ON to always put the erasing light source 35 in a standby state. The power consumption is reduced by turning ON the lamp 48 at the reduced power, and there are no undesirable effects on the stabilizing time of the lamp 48 by this reduction of power supplied to the lamp 48.

The excitation light (laser beam) emitted from the excitation light source 36 is deflected by the polygon mirror 37 and is irradiated on the photostimulated phosphor plate 33 so as to scan the photostimulated phosphor plate 33 in the main scan direction B. In this state, the precision stage 32 moves the photostimulated phosphor plate 33 in the direction A, which is perpendicular to the main scan direction B, so that the excitation light scans the entire photostimulated phosphor plate 33. The photostimulated luminescence light generated by one scan of the excitation light is converged by the optical guide path 40 and is supplied to the photo-multiplier 42 via the filter 41. The filter 41 provided between the optical guide path 40 and the photo-multiplier 42 does not pass the light having the wavelength of the excitation light and, instead passes the light having the wavelength of the photostimulated luminescence light.

The photostimulated luminescence light that is selectively obtained by the filter 41 is converted into an electrical signal in the photo-multiplier 42, and is supplied to the processing unit 43. More particularly, the electrical signal is amplified in the amplifier 44 of the processing unit 43 to an optimum signal level for the A/D converter 45. Output digital image data of the A/D converter 45 are stored in the memory 46. The stored digital image data are subjected to image processing in the image processor 47 and displayed on a CRT (not shown) or are output as a hard copy.

Next, as shown in FIG. 7B, the moving unit 34a (i.e., as seen in FIG. 4) moves the excitation light scan unit 34 to a position outside, (i.e., displaced from) the photostimulated phosphor plate 33. In this state, the lamp 48 of the erasing light source 35 is turned ON by the irradiation controller 51, and the irradiation controller 51 opens the shutter 50 to expose the light emission opening 49a. As a result, the erasing light from the lamp 48 irradiate's the entire surface of the photostimulated phosphor plate 33 and erases the residual radiation energy. In other words, by irradiating, on the photostimulated phosphor plate, 33 the erasing light having the major portion of the spectral distribution in the visible light region, it is possible to efficiently carry out the erasing process in a short time, that is, without requiring a long time for the erasing process.

Figure 8:
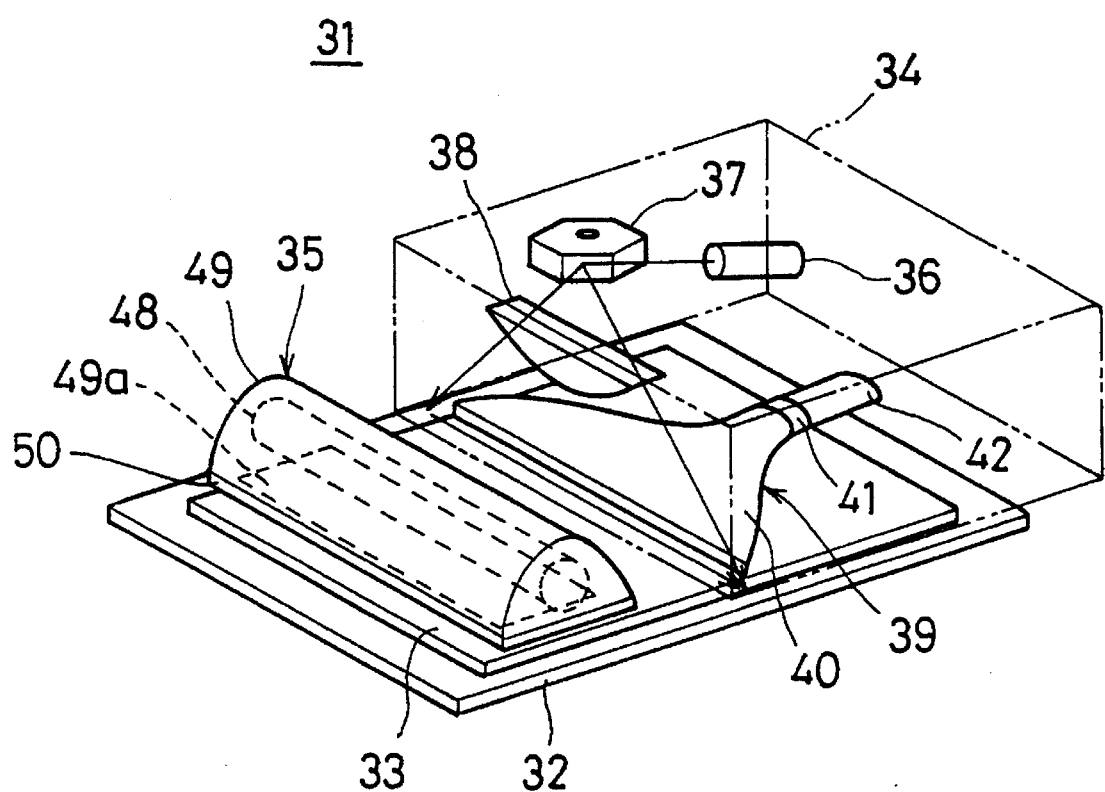
FIG. 8 is a perspective view generally showing a second embodiment of the radiation image reading apparatus according to the present invention.

Next, a description will be given of a second embodiment of the radiation image reading apparatus according to the present invention, by referring to FIG. 8. FIG. 8 generally shows the construction of the second embodiment. In FIG. 8, those parts which are the same as those corresponding parts in FIG. 4 are designated by the same reference numerals, and a description thereof will be omitted.

Figure 9A:
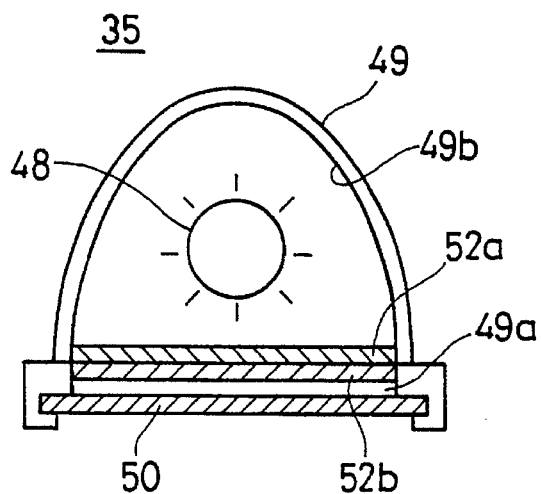
FIGS. 9A and 9B respectively are cross sectional views for explaining an erasing light source shown in FIG. 8.
Figure 9B:
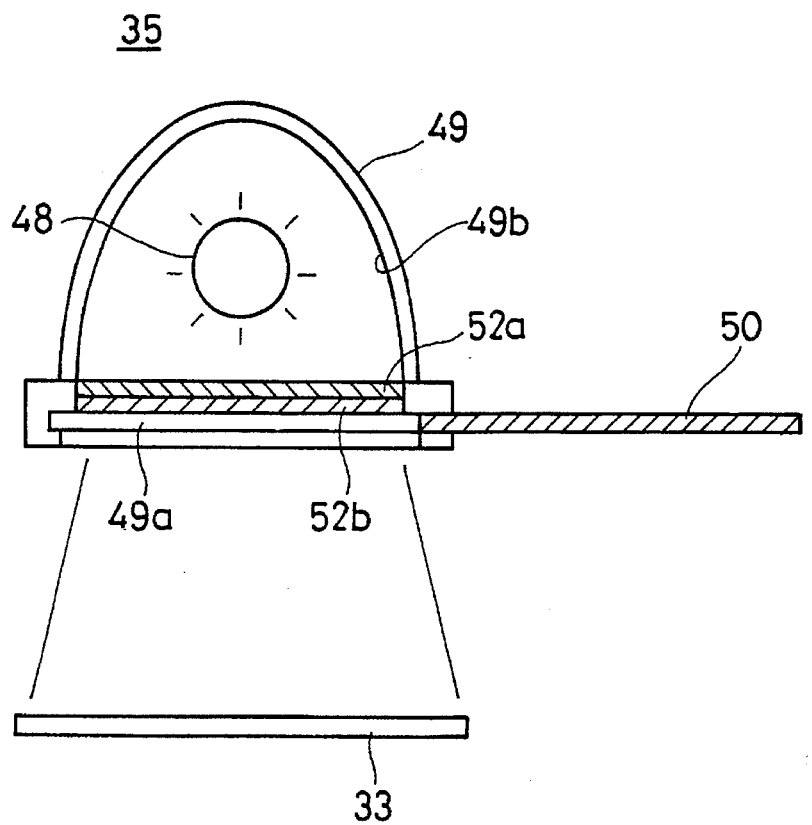

In the radiation image reading apparatus 31 shown in FIG. 8, the erasing light source 35 is arranged in parallel with the excitation light scan unit 34 on the photostimulated phosphor plate 33. Hence, the moving unit 34a shown in FIG. 4 is omitted in this embodiment. In addition, are infrared ray cutting filter 52a and an ultraviolet ray cutting filter 52b which are not; shown in FIG. 8 are provided at the light emission opening 39a of the erasing light source 35, as shown in FIGS. 9A and 9B which will be described later. Otherwise, the construction shown in FIG. 8 is basically the same as that shown in FIG. 4.

FIGS. 9A and 9B show cross sectional views of the erasing light source 35 shown in FIG. 8. FIG. 9A shows the erasing light source 35 in a state where the shutter 50 is closed, and FIG. 9B shows the erasing light source 35 in a state where the shutter 50 is open. As shown in FIGS. 9A and 9B, the infrared ray cutting filter 52a and the ultraviolet ray cutting filter 52b of the erasing light source 35 are provided at the light emission opening 49a of the light blocking member 49, on the inner side of the shutter 50.

Figure 10A:
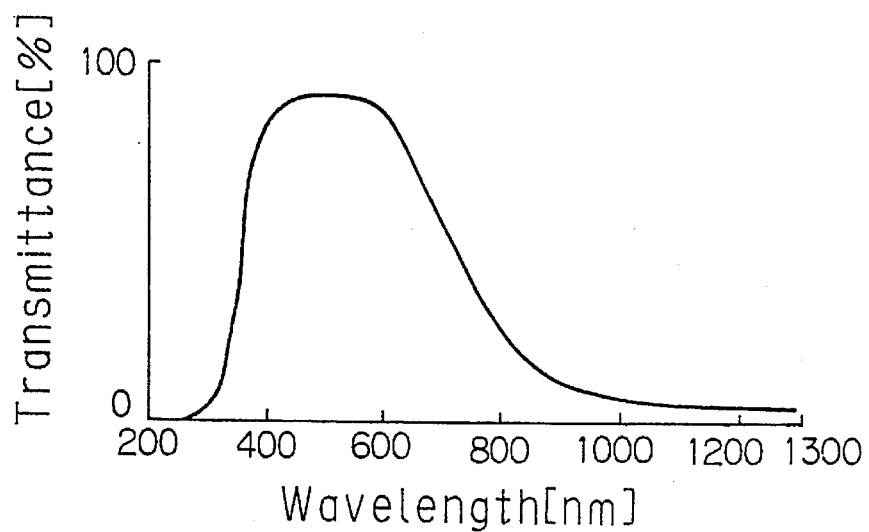
FIGS. 10A and 10B respectively are graphs for explaining filter characteristics of an infrared ray cutting filter shown in FIGS. 9A and 9B.
Figure 10B:
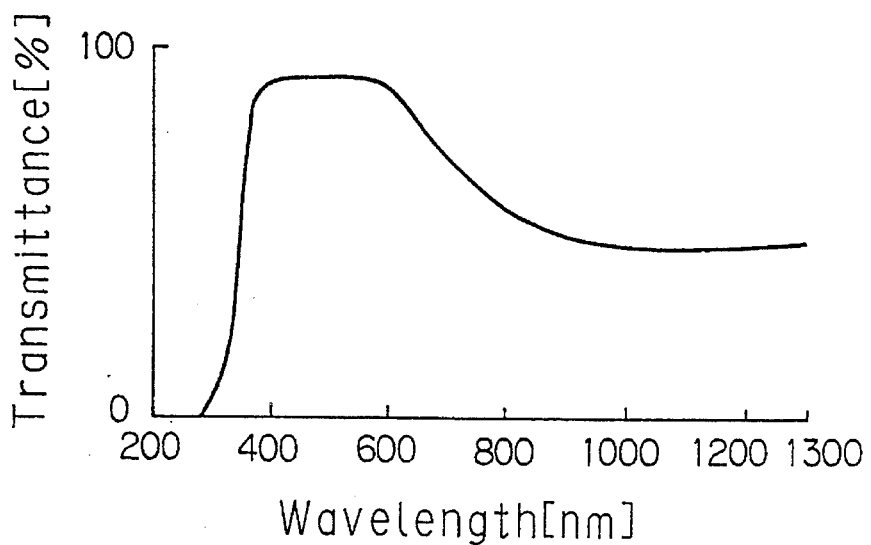

FIGS. 10A and 10B are graphs showing filter characteristics of the infrared ray cutting filter 52a. FIG. 10A shows the filter characteristic when a heat absorbing filter HA-50 (phosphate glass) manufactured by Hoya of Japan is used for the infrared ray cutting filter 52a, and FIG. 10B shows the filter characteristic when a heat absorbing filter HA-60 (silicate glass) manufactured by Hoya of Japan is used for the infrared ray cutting filter 52a. The heat absorbing filters HA-50 and HA-60 have a high transmittance in the visible light region and absorb heat in a very satisfactory manner, thereby making these filters well-suited for use as the infrared ray cutting filter 52a. In other words, filters having a high transmittance in the visible light region and a satisfactory heat absorbing characteristic are suited for use as the infrared ray cutting filter 52a.

Figure 11A:
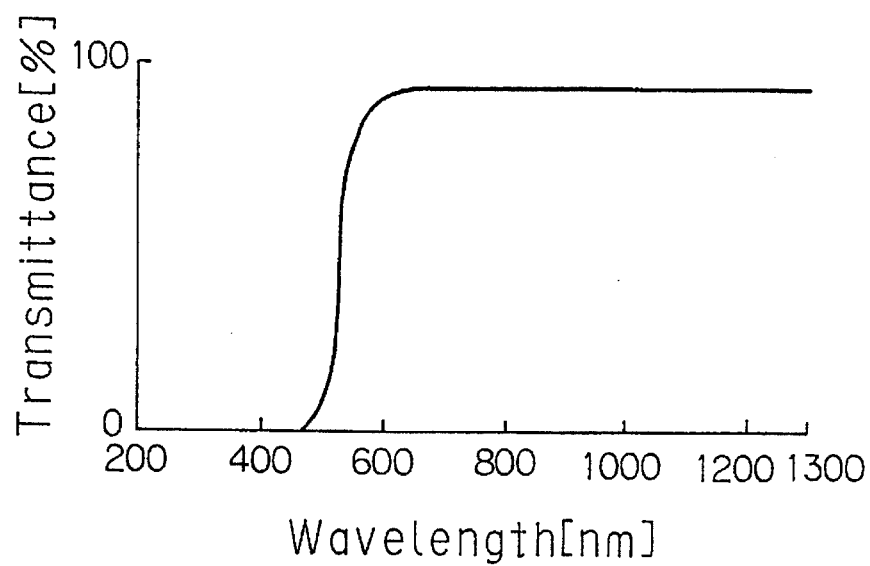
FIG. 11A is a graph for explaining filter characteristics of an ultraviolet ray cutting filter shown in FIGS. 9A and 9B.

On the other hand, FIG. 11A is a graph showing filter characteristics of the ultraviolet ray cutting filter 52b. FIG. 11A shows the filter characteristic when a sharp cut filter Y-44 (coloring glass) manufactured by Hoya of Japan is used for the ultraviolet ray cutting filter 52b. Filters such as an interference filter having an evaporation multi-layer structure are suited for use as the ultraviolet ray cutting filter 52b.

Returning now to the description of FIGS. 9A and 9B, the shutter 50 is closed as shown in FIG. 9A at times other than the time of the erasure, so that the erasing light will not be irradiated on the photostimulated phosphor plate 33. In this state where the shutter 50 is closed, the lamp 48 is controlled by the irradiation controller 51 so that the lamp 40 is turned ON at the reduced power. In other words, the control of the open/closed state of the shutter 50 and the switching of the power supply to the lamp 48 are linked. This linked control may be applied similarly to the embodiments described later.

On the other hand, at the time of the erasure, the shutter 50 is opened as shown in FIG. 9B. Hence, the erasing light from the lamp 48 passes through the infrared ray cutting filter 52a and the ultraviolet ray cutting filter 52b and is irradiated on the photostimulated phosphor plate 33 so as to eliminate the residual radiation energy.

There are cases where the light in the infrared ray region is slightly included in the components of the erasing light emitted from the lamp 48. Such light in the infrared light region will cause undesirable thermal effects when the heat resistance of the photostimulated phosphor plate 33 is low, and the infrared ray cutting filter 52a is provided to prevent such undesirable thermal effects. On the other hand, if the erasing light emitted from the lamp 48 even slightly includes the ultraviolet ray, this would cause undesirable effects on the erasure of the radiation energy and, thus, the ultraviolet ray cutting filter 52b is provided to prevent such undesirable effects on the erasure.

Figure 11B:
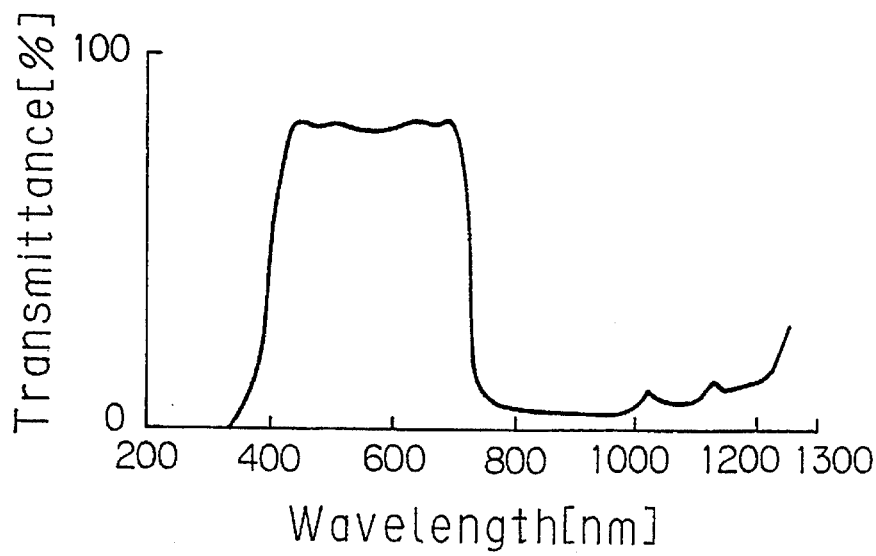
FIG. 11B is a graph for explaining filter characteristic of a bandpass filter.

Of course, a single bandpass filter which passes only the light in the visible light region may be provided in place of the infrared ray cutting filter 52a and the ultraviolet ray cutting filter 52b. In this case, the bandpass filter may have filter characteristics shown in FIG. 11B. FIG. 11B shows the filter characteristic when a dielectric multi-layer coating filter is used as the bandpass filter.

In the first and second embodiments described above, it is also possible to keep the photostimulated phosphor plate 33 fixed, and move the excitation light scan unit 34 and the erasing light source 35 in the moving direction A shown in FIG. 4. In other words, any arrangement may be employed as long as the photostimulated phosphor plate 33 moves relative to the excitation light scan unit 34 and the erasing light source 35 in the moving direction A.

Figure 12A:
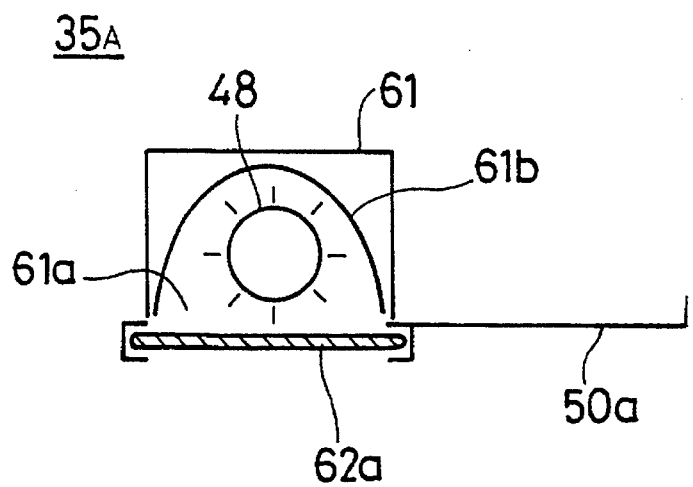
FIGS. 12A and 12B respectively are diagrams generally showing the construction of an erasing light source of a third embodiment of the radiation image reading apparatus according to the present invention.
Figure 12B:
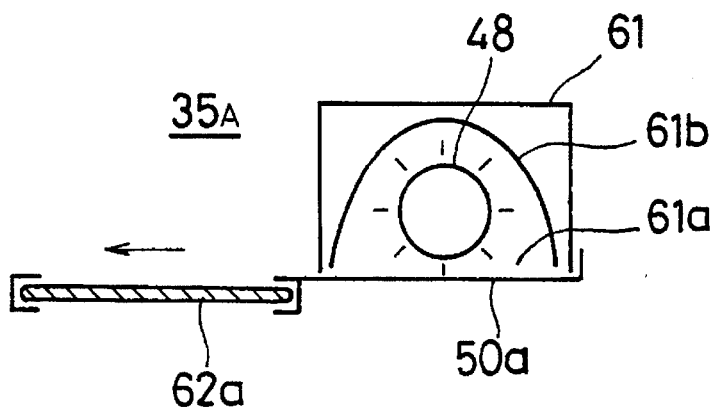

Next, a description will be given of a third embodiment of the radiation image reading apparatus according to the present invention, by referring to FIGS. 12A and 12B. FIG. 12A shows a cross section of an erasing light source of the third embodiment in a state where a shutter is open, and FIG. 12B shows a cross section of the erasing light source of the third embodiment in a state where the shutter is closed. In FIGS. 12A and 12B, those parts which are the same as those corresponding parts in FIGS. 9A and 9B are designated by the same reference numerals, and a description thereof will be omitted.

In FIGS. 12A and 12B, an erasing light source $35_A$ has the lamp 48 provided on the inside of a light blocking member 61 which has a light emission opening 61b. A reflecting mirror 61a is provided on the inside of the light blocking member 61 surrounding outside of the lamp 48. A shutter 50a and a bandpass filter 62a, for transmitting only the light in the visible light region, are integrally provided in parallel at the light emission opening 61a. The shutter 50a and the bandpass filter 62a are slidable in the horizontal direction as indicated by an arrow in FIG. 12B. Of course, a combination of the infrared ray cutting filter 52a and the ultraviolet ray cutting filter 52b described above may be provided in place of the bandpass filter 62a.

At the time of the erasure, the bandpass filter 62a is positioned at the light emission opening 61a as shown in FIG. 12A. On the other hand, at times other than the time of the erasure, the shutter 50a is slid to the position of the light emission opening 61a as shown in FIG. 12B. Accordingly, it is possible to avoid undesirable thermal effects on the bandpass filter 62a even though the lamp 48 is constantly turned ON. This erasing light source $35_A$ has a simple construction and can be manufactured at a low cost.

Figure 13A:
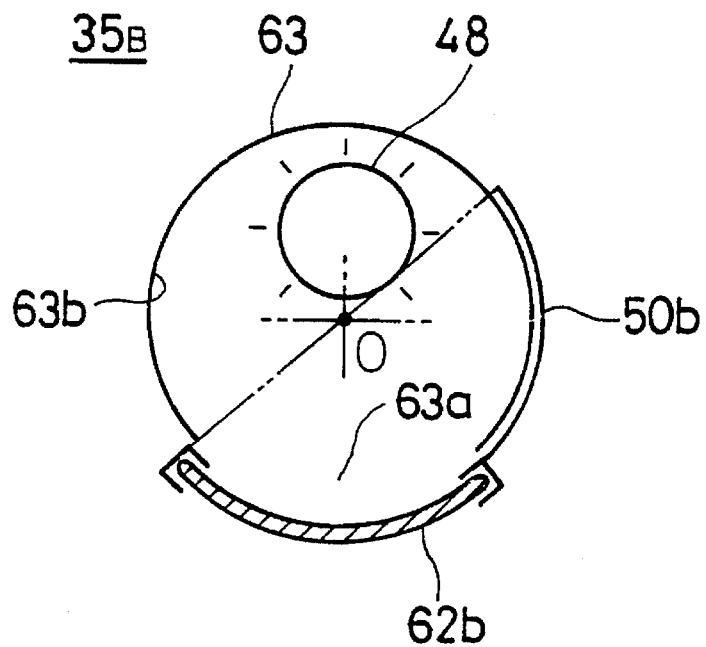
FIGS. 13A and 13B respectively are diagrams generally showing the construction of an erasing light source of a fourth embodiment of the radiation image reading apparatus according to the present invention.
Figure 13B:
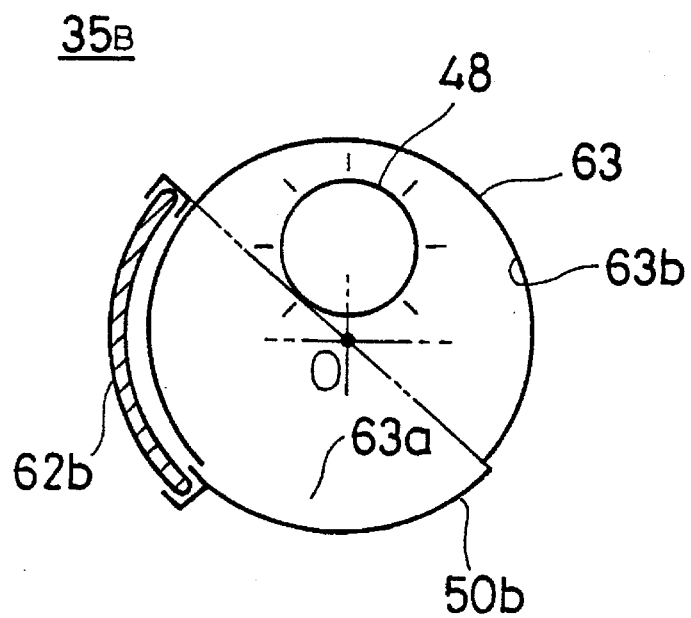

Next, a description will be given of a fourth embodiment of the radiation image reading apparatus according to the present invention, by referring to FIGS. 13A and 13B. FIG. 13A shows a cross section of an erasing light source of the fourth embodiment in a state where a shutter is open, and FIG. 13B shows a cross section of the erasing light source of the fourth embodiment in a state where the shutter is closed. In FIGS. 13A and 13B, those parts which are the same as those corresponding parts in FIGS. 9A and 9B are designated by the same reference numerals, and a description thereof will be omitted.

In FIGS. 13A and 13B, an erasing light source $35_B$ has the lamp 48 provided on the inside of a light blocking member 63 which has a light emission opening 63a. The light blocking member 63 has a generally circular shape in the cross sectional view, and a reflecting mirror 63b is integrally provided on the inner side of the light blocking member 63. The lamp 48 is arranged at a position deviated from a center O of the light blocking member 63 in a direction further away from the light emission opening 63a.

An arcuate bandpass filter 62b and an arcuate shutter 50b are integrally provided in parallel with a radius of curvature approximately the same as that of the light blocking member 63. The bandpass filter 62b and the shutter 50b can turn about the center line, or axis, O of the number 63. In other words, the bandpass filter 62b is turned to the rotary position at the light emission opening 63a as shown in FIG. 13A at the time of the erasure, and the shutter 50b is turned to the rotary position at the light emission opening 63a as shown in FIG. 13B at times other than the time of the erasure.

Accordingly, it is possible to avoid the undesirable thermal effects on the bandpass filter 62b even though the lamp 48 is constantly turned ON. In addition, the space occupied by the shutter 50b and the bandpass filter 62b becomes small, thereby making it possible to reduce the size of the reading apparatus.

Figure 14A:
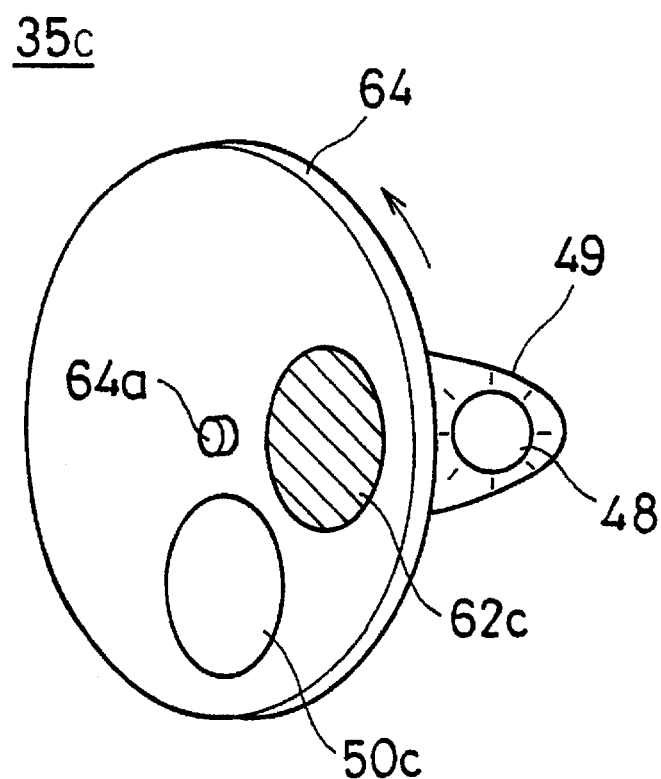
FIGS. 14A and 14B respectively are diagrams generally showing the construction of an erasing light source of a fifth embodiment of the radiation image reading apparatus according to the present invention.
Figure 14B:
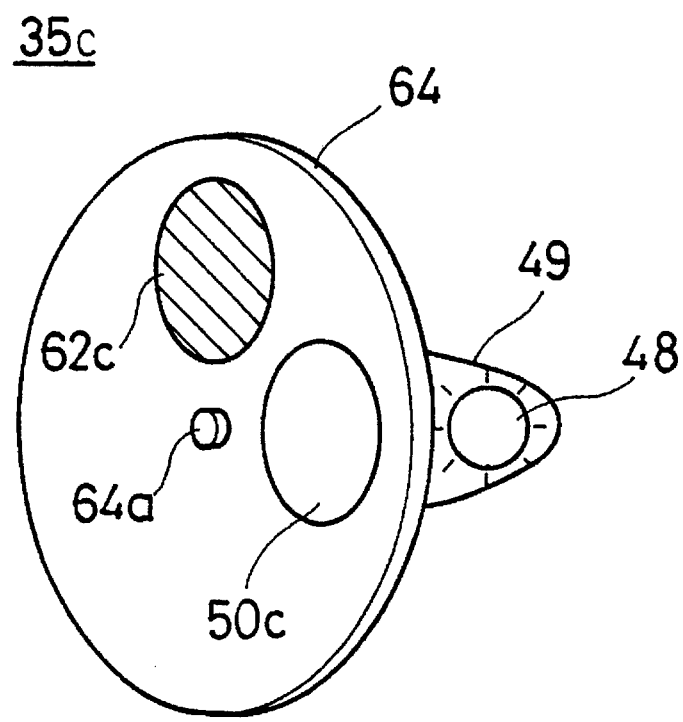

Next, a description will be given of a fifth embodiment of the radiation image reading apparatus according to the present invention, by referring to FIGS. 14A and 14B. FIG. 14A shows a perspective view of an erasing light source of the fifth embodiment in a state where a shutter is open, and FIG. 14B shows a perspective view of the erasing light source of the fifth embodiment in a state where the shutter is closed. In FIGS. 14A and 14B, those parts which are the same as those corresponding parts in FIGS. 9A and 9B are designated by the same reference numerals, and a description thereof will be omitted.

In FIGS. 14A and 14B, an erasing light source $35_C$ has the lamp 48 provided on the inside of the light blocking member 49 which has the light emission opening 49a (not shown in FIGS. 14A and 14B). A disk 64 rotatable about a shaft 64a is arranged in front of the light emission opening 49a of the light blocking member 49. A shutter 50c and a bandpass filter 62c having approximately the same shape as the light emission opening 49a are provided on the disk 64. For example, the shutter 50c and the bandpass filter 62c are embedded in the disk 64. Of course, the shape of the shutter 50c and the bandpass filter 62c is not limited to the circular shape shown in FIGS. 14A and 14B.

At the time of the erasure, the disk 64 is rotated to the rotary position shown in FIG. 14A, so that the bandpass filter 62c confronts the light emission opening 49a. On the other hand, at times other than the time of the erasure, the disk 64 is rotated to the rotary position shown in FIG. 14B, so that the shutter 50c confronts the light emission opening 49a. Accordingly, it is possible to avoid the undesirable thermal effects on the bandpass filter 62c even though the lamp 48 is constantly turned ON.

If the disk 64 is made of a non-transparent material, all of the portions of the disk 64 other than the bandpass filter 62c will function as the shutter and it is unnecessary to provide the shutter 50c. In addition, since the disk 64 is merely used to alternately switch the portion confronting the light emission opening 49a between the bandpass filter 62c and the shutter 50c, it is possible to use a member having a shape other than the disk shape for carrying the bandpass filter 62c and the shutter 50c. For example, such a member may have a fan shape. Further, it is of course possible to provide a plurality of bandpass filters 62c and shutters 50c if necessary.

Figure 15A:
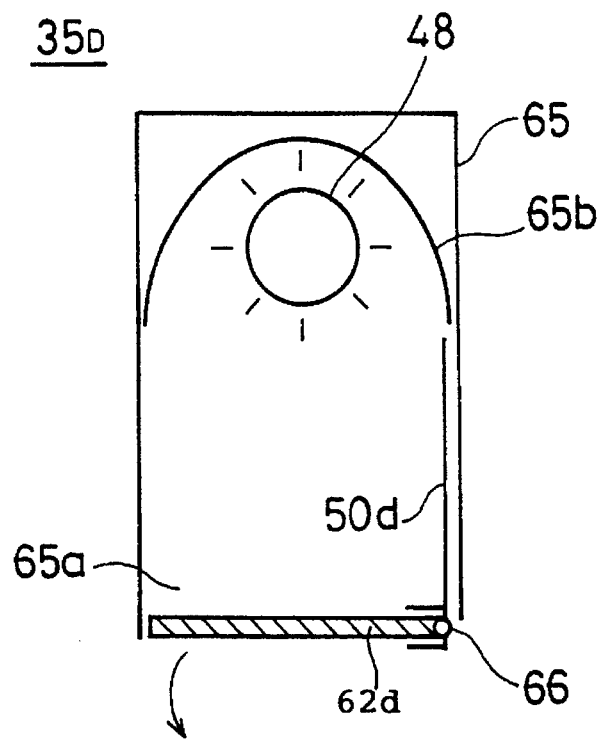
FIGS. 15A and 15B respectively are diagrams generally showing the construction of an erasing light source of a sixth embodiment of the radiation image reading apparatus according to the present invention.
Figure 15B:
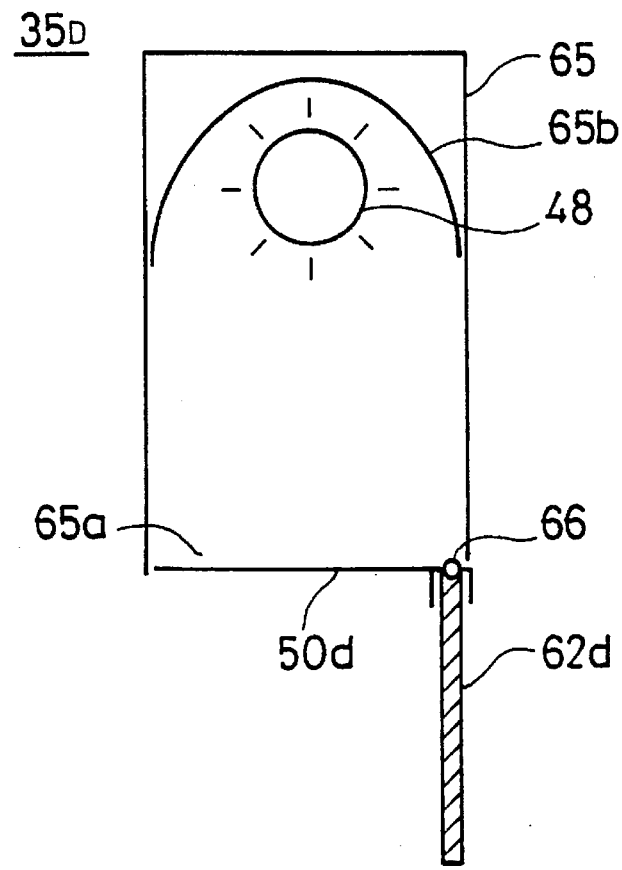

Next, a description will be given of a sixth embodiment of the radiation image reading apparatus according to the present invention, by referring to FIGS. 15A and 15B. FIG. 15A shows a cross section of an erasing light source of the sixth embodiment in a state where a shutter is open, and FIG. 15B shows a cross section of the erasing light source of the sixth embodiment in a state where the shutter is closed. In FIGS. 15A and 15B, those parts which are the same as those corresponding parts in FIGS. 9A and 9B are designated by the same reference numerals, and a description thereof will be omitted.

In FIGS. 15A and 15B, an erasing light source $35_D$ has an elongated rectangular box-shaped light blocking member 65 having a light emission opening 65a provided at one end thereof. A reflecting mirror 65b and the lamp 48 are provided in the inner part (top portion in FIGS. 15A and 15B) of the light blocking member 65.

A shutter 50d and a bandpass filter 62d are connected in an L-shape, and is pivotally supported on a shaft 66 at a predetermined position within the light emission opening 65a of the light blocking member 65. In other words, at the time of the erasure, the shutter 50d is open and the bandpass filter 62d is located at the light emission opening 65a as shown in FIG. 15A. On the other hand, at times other than the time of the erasure, the shutter 50d and the bandpass filter 62d are pivoted so that the shutter 50d closes the light emission opening 65a as shown in FIG. 15B. As a result, it is possible to avoid the undesirable thermal effects on the bandpass filter 62d even though the lamp 48 is constantly turned ON.

In this case, the reflecting mirror 65b and the lamp 48 are provided at the inner part of the light blocking member 65, so that there is sufficient space to accommodate the shutter 50d in the open state of the shutter 50d. In addition, a space must be provided to allow the bandpass filter 62d to recede when the shutter 50d is closed.

Figure 16A:
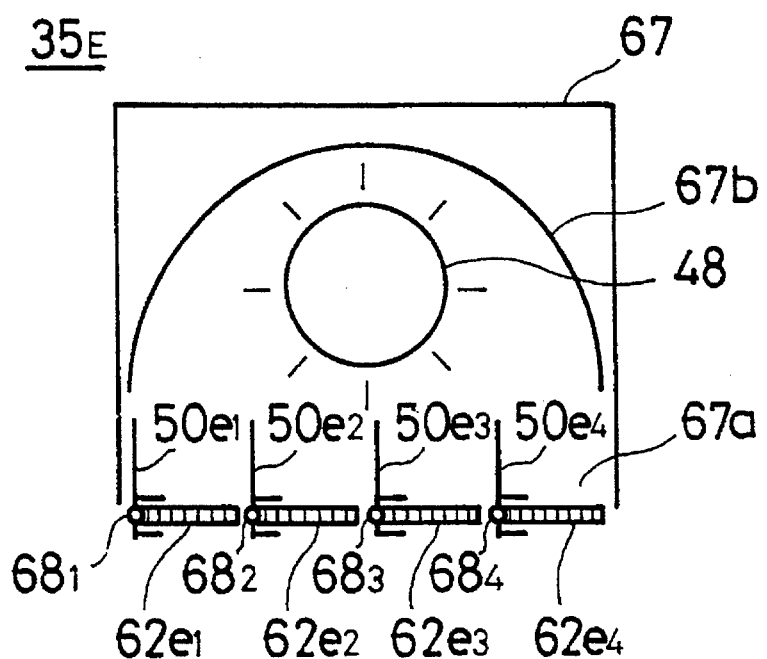
FIGS. 16A and 16B respectively ape diagrams generally showing the construction of an erasing light source of a seventh embodiment of the radiation image reading apparatus according to the present invention.
Figure 16B:
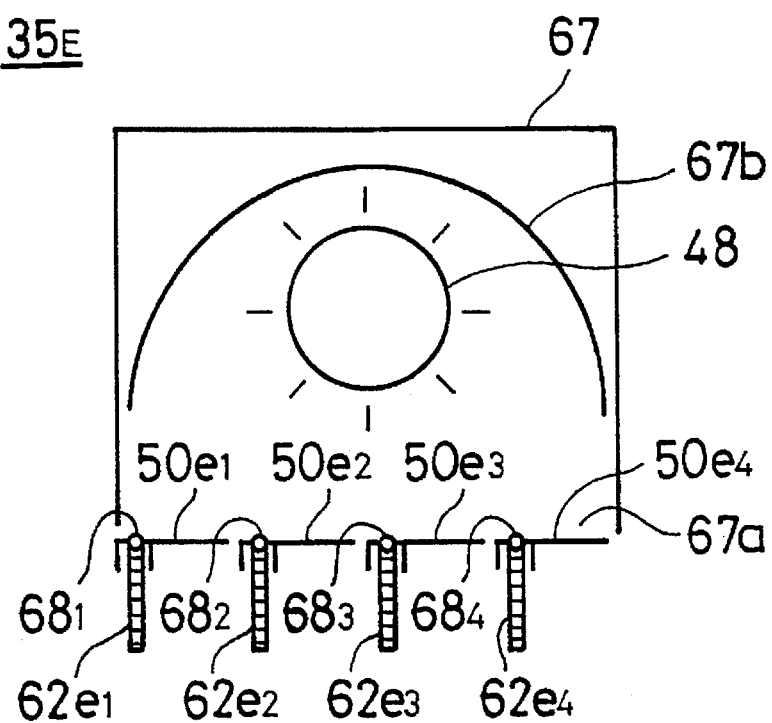

Next, a description will be given of a seventh embodiment of the radiation image reading apparatus according to the present invention, by referring to FIGS. 16A and 16B. FIG. 16A shows a cross section of an erasing light source of the seventh embodiment in a state where shutters are open, and FIG. 16B shows a cross section of the erasing light source of the seventh embodiment in a state where the shutters are closed. In FIGS. 16A and 16B, those parts which are the same as those corresponding parts in FIGS. 9A and 9B are designated by the same reference numerals, and a description thereof will be omitted.

In FIGS. 16A and 16B, an erasing light source $35_E$ has a rectangular box-shaped light blocking member 67 having a light emission opening 67a at one end thereof. A reflecting mirror 67b and the lamp 48 are provided on the inner part of the light blocking member 67.

A shutter 50ei and a bandpass filter 62ei are connected in an L-shape, and the structure is pivotally supported on a shaft $68_i$ at a predetermined position within the light emission opening 67a of the light blocking member 67, where i=1, 2, 3, 4. Both the shutter 50ei and the bandpass filter 62ei are small compared to the shutter 50d and the bandpass filter 62d of the sixth embodiment described above. The four (i.e., 4) shutter-bandpass filter combinations are arranged without a gap therebetween, and so as to cover fully the light emission opening 67a. Of course, the number of such shutter-bandpass filter combinations is not limited to four.

At the time of the erasure, the shutters 50e1 through 50e4 are open and the bandpass filters 62e1 through 62e4 are located at the light emission opening 67a as shown in FIG. 16A. On the other hand, at times other than the time of the erasure, the shutters 50e1 through 50e4 and the bandpass filters 62e1 through 62e4 are pivoted so that the shutters 50e1 through 50e4 close the light emission opening 67a as shown in FIG. 16B. In other words, in this embodiment, the shutters 50e1 through 50e4 and the corresponding bandpass filters 62e1 through 62e4 are linked so as to pivot simultaneously in synchronism with each other. As a result, it is possible to avoid the undesirable thermal effects on the bandpass filters 62e1 through 62e4 even though the lamp 48 is constantly turned ON.

In this case, it is possible to reduce the size of the reading apparatus; compared to the sixth embodiment, because the space necessary to pivot the shutter-bandpass filter combinations is smaller than that required in the sixth embodiment.

In each of the embodiments described above, the erasing light source only uses a single lamp. However, it is possible to use a plurality of lamps as long as the light irradiated on the photostimulated phosphor plate 33 for the erasure has the spectral distribution in the visible light region or its vicinity.

Further, the present invention is not limited to these embodiments, but various variations and modifications may be made without departing from the scope of the present invention.

What is claimed is:

1. A radiation image reading apparatus operable in an alternating sequence of image reading and erasing, comprising:

a photostimulated phosphor member which absorbs a portion of radiation energy, transmitted through an object and incident thereon, and stores the absorbed radiation energy in a form of a latent image;

an excitation light source irradiating an excitation light onto said photostimulated phosphor member in a main scan direction so as to generate the emission of photostimulated luminescence light corresponding to the latent image from said photostimulated phosphor member;

an image reading unit for receiving and converging the photostimulated luminescence light emission from said photostimulated phosphor member and thereby reading image information of the latent image, which is dependent on light intensity of the corresponding photostimulated luminescence light, and outputting a corresponding electrical signal;

an erasing light source producing an irradiating erasing light for erasing residual, stored radiation energy of the latent image remaining in said photostimulated phosphor member at an erasure time, after obtaining the image information of the latent image by said image reading unit, said irradiating erasing light of said erasing light source having a major part of a spectral distribution thereof within a band substantially of a visible light region and said erasing light source further comprising a lamp, a controller and a shutter, the controller maintaining the lamp in an ON condition during the alternating sequence of image reading and erasing but switching the lamp to a reduced power level at times other than when erasing residual radiation energy and controlling the shutter to be closed to prevent irradiating, and to be opened to permit irradiating, the erasing light onto the photostimulated phosphor member for erasing same; and a moving unit which moves said excitation light source and said image reading unit with respect to said photostimulated phosphor member in a moving direction which is perpendicular to the main scan direction.

2. The radiation image reading apparatus as claimed in claim 1, wherein said lamp is selected from a group consisting of a high-pressure sodium lamp, a low-pressure sodium lamp, a metal halide lamp and a mercury lamp.

3. The radiation image reading apparatus as claimed in claim 1, wherein said erasing light source further comprises:

a light blocking member having an end provided with a light emission opening, the lamp being provided inside the light blocking member and emitting the irradiating erasing light through the light emission opening for erasing; and said shutter is positioned at the light emission opening and is selectively closed by the controller to block the irradiating erasing light of the lamp from passing through the light emission opening at times other than when erasing the phosphor member.

4. The radiation image reading apparatus as claimed in claim 3, wherein said erasing light source further comprises:

a reflecting mirror provided inside the light blocking member, between the lamp and the light blocking member.

5. The radiation image reading apparatus as claimed in claim 3, wherein said erasing light source further comprises:

a filter positioned at the light emission opening and which cuts a selected one of infrared rays and ultraviolet rays from the irradiating erasing light, as emitted by the lamp and passing through the light emission opening and thereby the filter when the shutter is open.

6. The radiation image reading apparatus as claimed in claim 5, wherein said erasing light source further comprises:

linking means for linking the shutter and the filter for coordinated movement thereof relatively to the light emission opening, so that the shutter is positioned at and blocks the light emission opening when the shutter is closed and the filter is positioned at the light emission opening when the shutter is opened and displaced therefrom.

7. The radiation image reading apparatus as claimed in claim 6, wherein said linking means further comprises means for linearly moving the shutter and the filter relatively to the light emission opening.

8. The radiation image reading apparatus as claimed in claim 6, wherein said linking means further comprises means for mounting the shutter and the filter at respective, angularly displaced relative positions and for common pivotal movement, such that when the shutter is closed the shutter is positioned at and blocks the light emission opening and the filter is displaced therefrom, and such that when the shutter is opened the filter is located at the light emission opening and filters the irradiating erasing light passing through the light emission opening and the shutter is displaced therefrom.

9. The radiation image reading apparatus as claimed in claim 5, wherein said erasing light source further comprises a plurality of said shutters and a plurality of respective said filters.

10. The radiation image reading apparatus as claimed in claim 1, wherein the relative, respective positions of said photostimulated phosphor member and said erasing light source are fixed.

11. The radiation image reading apparatus as claimed in claim 1, which further comprises:

means for relatively moving said erasing light source with respect to said photostimulated phosphor member.

12. The radiation image reading apparatus as claimed in claim 1, wherein said controller, further, controls opened and closed states of said shutter in a linked manner to the control of said lamp.

13. The radiation image reading apparatus as claimed in claim 12, wherein a filter is connected integrally to said shutter.

14. A radiation image reading apparatus operable in an alternating sequence of image reading and erasing, comprising:

a photostimulated phosphor member which absorbs a portion of radiation energy, transmitted through an object and incident thereon, and stores the absorbed radiation energy in a form of a latent image;

an excitation light source irradiating an excitation light onto said photostimulated phosphor member in a main scan direction so as to generate the emission of photostimulated luminescence light corresponding to the latent image from said photostimulated phosphor member;

an image reading unit for receiving and converging the photostimulated luminescence light emission from said photostimulated phosphor member and thereby reading image information of the latent image, which is dependent on light intensity of the corresponding photostimulated luminescence light, and outputting a corresponding electrical signal;

an erasing light source producing an irradiating erasing light for erasing residual, stored radiation energy of the latent image remaining in said photostimulated phosphor member at an erasure time, after obtaining the image information of the latent image by said image reading unit, said irradiating erasing light of said erasing light source having a major part of a spectral distribution thereof within a band substantially of a visible light region and said erasing light source further comprising:

a light blocking member having an end provided with a plurality of light emission openings, a lamp provided inside the light blocking member and emitting the irradiating emission light through the plurality of light emission openings, a plurality of shutters respectively positioned at the plurality of light emission openings and selectively and commonly movable to closed positions, for blocking the respective light emission openings and thereby blocking the irradiating erasing light from passing through the respective light emission openings at times other than when irradiating the phosphor member for erasing, and to opened positions, for passing the irradiating erasing light through the respective light emission openings, and a plurality of common filters respectively corresponding to the plurality of emission openings and positioned thereat, at least in the opened positions of the corresponding plurality of shutters, for passing the irradiating erasing light therethrough, the plurality of filters commonly cutting a selected one of infrared rays and ultraviolet rays from the light emitted by the lamp and passing through the plurality of light emission openings and the corresponding filters when the respective plurality of shutters is opened.

15. The radiation image reading apparatus as claimed in claim 14, wherein said lamp is selected from a group consisting of a high-pressure sodium lamp, a low-pressure sodium lamp, a metal halide lamp and a mercury lamp.

16. The radiation image reading apparatus as claimed in claim 14, wherein said erasing light source further comprises:

a reflecting mirror provided inside the light blocking member, between the lamp and the light blocking member.

17. The radiation image reading apparatus as claimed in claim 14, wherein said erasing light source further comprises:

linking means for linking the plurality of shutters and the respective plurality of filters for coordinated movement relatively to the respective plurality of light emission openings, so that the plurality of shutters is positioned at and blocks the respective light emission openings when the plurality of shutters is closed and the plurality of filters is positioned at the respective light emission openings when the plurality of shutters is opened and displaced therefrom.

18. The radiation image reading apparatus as claimed in claim 17, wherein said linking means further comprises means for linearly moving the respective pluralities of shutters and filters, relatively to the respective plurality of light emission openings.

19. The radiation image reading apparatus as claimed in claim 17, wherein said linking means further comprises means for mounting the respective pluralities of shutters and filters at respective and common angularly displaced relative positions and for common pivotal movement, such that the plurality of shutters, when closed, is positioned at and blocks the respective light emission openings and the plurality of filters is displaced therefrom, and such that when the plurality of shutters is opened, the plurality of filters is located at the respective plurality of light emission openings and the plurality of shutters is displaced therefrom.

20. The radiation image reading apparatus as claimed in claim 14, wherein the relative, respective positions of said photostimulated phosphor member and said erasing light source are fixed.

21. The radiation image reading apparatus as claimed in claim 14, which further comprises:

means for relatively moving said erasing light source with respect to said photostimulated phosphor member.

22. A radiation image reading apparatus operable in an alternating sequence of image reading and erasing, comprising:

a photostimulated phosphor member which absorbs a portion of radiation energy, transmitted through an object and incident thereon and stores the absorbed radiation energy in a form of a latent image;

an excitation light source irradiating an excitation light onto said photostimulated phosphor member in a main scan direction so as to generate the emission of photostimulated luminescence light corresponding to the latent image from said photostimulated phosphor member;

an image reading unit for receiving and converging the photostimulated luminescence light emission from said photostimulated phosphor member and thereby reading image information of the latent image, which is dependent on light intensity of the corresponding photostimulated luminescence light, and outputting a corresponding electrical signal;

an erasing light source producing an irradiating erasing light for erasing residual, stored radiation energy of the latent image remaining in said photostimulated phosphor member at an erasure time, after obtaining the image information of the latent image by said image reading unit, said irradiating erasing light of said erasing light source having a major part of a spectral distribution thereof within a band substantially of a visible light region and said erasing light source further comprising:

a light blocking member having an end provided with a light emission opening, a lamp disposed inside the light blocking member and positioned relatively to the light emission opening for transmission of the irradiating erasing light therethrough, a shutter being positioned at the light emission opening, such that when the shutter is closed, the transmission through the opening is blocked, a filter provided at the light emission opening and cutting at least one of infrared rays and ultraviolet rays from the irradiating erasing light for transmission through the light emission opening when the shutter is open, and a controller which controls said lamp so that said lamp is turned ON with a reduced power at times other than during the erasure time, relatively to the power of said lamp as turned ON at the erasure time; and a moving unit which moves said excitation light source and said image reading unit with respect to said photostimulated phosphor member in a moving direction which is perpendicular to the main scan direction.

* * * * *

UNITED STATES PATENT AND TRADEMARK OFFICE
CERTIFICATE OF CORRECTION

PATENT NO. : 5,534,709
DATED : July 9, 1996
INVENTOR(S) : YOSHIMOTO et al.

It is certified that error appears in the above-indentified patent and that said Letters Patent is hereby corrected as shown below:

Col. 1, line 39, change "Where" to --where--.

Col. 2, line 20, change "creasing" to --erasing--;
line 44, change "performed" to --performs--.

Col. 4, line 12, change "light," to --light--;
line 27, change "time," to --time--;
line 41, change "image," to --image--.

Col. 5, line 20, change "ape" to --are--;
line 47, delete "is".

Col. 7, line 31, after "instead" insert --,--;
line 51, change "irradiate's" to --irradiates--.

Col. 8, line 3, change "are" to --an--;
line 5, change "not;" to --not--.

Col. 9, line 32, change "61b" to --61a--;
line 33, change "61a" to --61b--;
line 34, after "surrounding" insert --the--.

Col. 12, line 11, change "apparatus;" to --apparatus--.

Col. 16, line 30, change "opening," to --opening--.

Signed and Sealed this

Seventeenth Day of December, 1996

Attest:

BRUCE LEHMAN

Attesting Officer        Commissioner of Patents and Trademarks